US010712879B2

(12) United States Patent
Zhou et al.

(10) Patent No.: US 10,712,879 B2
(45) Date of Patent: Jul. 14, 2020

(54) TOUCH CAPACITANCE TRANSDUCED ENERGY HARVESTING SYSTEM

(71) Applicant: The Regents of the University of California, Oakland, CA (US)

(72) Inventors: Alyssa Zhou, Berkeley, CA (US); Michel Maharbiz, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 577 days.

(21) Appl. No.: 15/623,495

(22) Filed: Jun. 15, 2017

(65) Prior Publication Data

US 2018/0364831 A1    Dec. 20, 2018

(51) Int. Cl.
| | | |
|---|---|---|
| *G06F 3/00* | (2006.01) | |
| *H02N 1/08* | (2006.01) | |
| *G06F 3/044* | (2006.01) | |
| *G06F 3/041* | (2006.01) | |
| *B60L 53/51* | (2019.01) | |
| *H01G 5/16* | (2006.01) | |

(Continued)

(52) U.S. Cl.
CPC .............. *G06F 3/044* (2013.01); *B60L 53/51* (2019.02); *G06F 1/3262* (2013.01); *G06F 3/0416* (2013.01); *H01G 5/16* (2013.01); *H02N 1/08* (2013.01); *A61B 5/6801* (2013.01)

(58) Field of Classification Search
CPC ...... G06F 3/044; G06F 1/3262; G06F 3/0416; B60L 53/51; H01G 5/16; H02N 11/00; A61B 5/6801
USPC ................................................ 310/308, 309
See application file for complete search history.

(56) References Cited

U.S. PATENT DOCUMENTS 6,479,920 B1 *  11/2002  Lal .......................... G21H 1/00
                                                    310/309
7,851,968 B2 *  12/2010  Chaillout ................. H02N 1/08
                                                    310/308

(Continued)

OTHER PUBLICATIONS

Arias, Ana Claudia et al., "Materials and Applications for Large Area Electronics: Solution-Based Approaches," Chemical Reviews, vol. 110, Issue 1, Jan. 13, 2010, American Chemical Society, pp. 3-24.

(Continued)

*Primary Examiner* — Thomas M Dougherty
(74) *Attorney, Agent, or Firm* — Withrow & Terranova, P.L.L.C.

(57) ABSTRACT

Aspects disclosed in the detailed description include a touch capacitance transduced energy harvesting system. The energy harvesting system includes a touch sensing electrode array and energy harvesting circuitry coupled to the touch sensing electrode array. When a movable conductive object (e.g., a human finger) moves toward or away from the touch sensing electrode array, capacitance of the touch sensing electrode array increases and decreases accordingly, thus transducing a direct current (DC) current in the touch sensing electrode array. As such, the energy harvesting circuitry can be configured to harvest electric energy from the DC current to generate and store a DC voltage. By harvesting the electric energy transduced from the kinetic energy of the movable conductive object, it is possible to power a low-power electronic device (e.g., a biosensor) with motions already used for interfacing with the low-power electronic device.

20 Claims, 8 Drawing Sheets

(51) Int. Cl.
G06F 1/3234 (2019.01)
A61B 5/00 (2006.01)

(56) References Cited

U.S. PATENT DOCUMENTS

| | | | | |
|---|---|---|---|---|
| 9,184,675 | B1* | 11/2015 | Dea | H02N 1/00 |
| 9,431,929 | B2* | 8/2016 | Nishida | H02N 2/186 |
| 2009/0140443 | A1* | 6/2009 | Hohlfeld | H02N 1/08 257/786 |
| 2012/0181897 | A1* | 7/2012 | Masaki | H02N 1/08 310/309 |
| 2012/0181901 | A1* | 7/2012 | Krupenkin | H01G 5/012 310/339 |
| 2013/0134830 | A1* | 5/2013 | Ikuta | H02N 1/08 310/309 |
| 2013/0208397 | A1* | 8/2013 | Benslimane | H01G 5/16 361/280 |
| 2014/0077657 | A1* | 3/2014 | Nakatsuka | H02N 1/10 310/309 |
| 2015/0001991 | A1* | 1/2015 | Ardanuc | H02N 1/00 310/309 |
| 2015/0145333 | A1* | 5/2015 | Masaki | H02N 1/08 307/31 |
| 2015/0236619 | A1* | 8/2015 | Hattori | H02N 1/08 310/309 |
| 2016/0118912 | A1* | 4/2016 | Hayashi | B81C 99/002 310/309 |
| 2019/0058420 | A1* | 2/2019 | Toshiyoshi | H02N 1/08 |

OTHER PUBLICATIONS

Beeby, S. P. et al., "Energy harvesting vibration sources for microsystems applications," Measurement Science and Technology, vol. 17, Issue 12, Oct. 26, 2006, IOP Publishing Ltd, pp. R175-R195.

Borno, Ruba T. et al., "Charge-pumping in a synthetic leaf for harvesting energy from evaporation-driven flows," Applied Physics Letters, vol. 95, Issue 1, Jul. 7, 2009, American Institute of Physics, pp. 013705-1 through 013705-3.

Chen, Ting et al., "A Miniature Biofuel Cell," Journal of the American Chemical Society, vol. 123, Issue 35, 2001, American Chemical Society, pp. 8630-8631.

Evans, Dave, "The Internet of Things: How the Next Evolution of the Internet Is Changing Everything," White Paper, Apr. 2011, Cisco IBSG, pp. 1-11.

Gorlatova, Maria et al., "Movers and Shakers: Kinetic Energy Harvesting for the Internet of Things," ACM Sigmetrics Performance Evaluation Review—Performance evaluation review, vol. 42, Issue 1, Jun. 2014, ACM, pp. 1-16.

Gubbi, Jayavardhana et al., "Internet of Things (IoT): A vision, architectural elements, and future directions," Future Generation Computer Systems, vol. 29, Issue 7, Feb. 24, 2013, Elsevier B.V., pp. 1645-1660.

Harne, R. L. et al., "A review of the recent research on vibration energy harvesting via bistable systems," Smart Materials and Structures, vol. 22, Issue 2, Jan. 25, 2013, IOP Publishing Ltd, pp. 1-12.

Hoang, D.C. et al., "Thermal Energy Harvesting From Human Warmth for Wireless Body Area Network in Medical Healthcare System," International Conference on Power Electronics and Drive Systems (PEDS), Jan. 2-5, 2009, Taipei, Taiwan, IEEE, pp. 1277-1282.

Jayakumar, Hrishikesh et al., "Powering the Internet of Things," International Symposium on Low Power Electronics and Design, Aug. 11-13, 2014, La Jolla, CA, USA, ACM, pp. 375-380.

Jiang, C. Y. et al., "High-bendability flexible dye-sensitized solar cell with a nanoparticle-modified ZnO-nanowire electrode," Applied Physics Letters, vol. 92, Issue 14, Apr. 7, 2008, American Institute of Physics, pp. 143101-1 through 143101-3.

Kim, Hyug-Han et al., "A Miniature Membrane-less Biofuel Cell Operating under Physiological Conditions at 0.5 V," Journal of The Electrochemical Society, vol. 150, Issue 2, 2003, The Electrochemical Society, p. A209-A213.

Kim, Heung Soo et al., "A Review of Piezoelectric Energy Harvesting Based on Vibration," International Journal of Precision Engineering and Manufacturing, vol. 12, Issue 6, Dec. 2011, KSPE and Springer, pp. 1129-1141.

Kymissis, John et al., "Parasitic Power Harvesting in Shoes," Second International Symposium on Wearable Computers, Oct. 19-20, 1998, Pittsburgh, PA, USA, IEEE, 8 pages.

Meninger, Scott et al., "Vibration-to-Electric Energy Conversion," IEEE Transactions on Very Large Scale Integration (VLSI) Systems, vol. 9, Issue 1, Feb. 2001, IEEE, pp. 64-76.

Ostfeld, Aminy E. et al., "Screen printed passive components for flexible power electronics," Scientific Reports, vol. 5, Oct. 30, 2015, www.nature.com/scientificreports/, Nature Publishing Group, pp. 1-11.

Park, Steve et al., "Stretchable Energy-Harvesting Tactile Electronic Skin Capable of Differentiating Multiple Mechanical Stimuli Modes," Advanced Materials, vol. 26, Issue 43, 2014, WILEY-VCH Verlag GmbH & Co., pp. 1-9.

Raghunathan, Vijay et al., "Emerging Techniques for Long Lived Wireless Sensor Networks," IEEE Communications Magazine, vol. 44, Issue 4, Apr. 2006, IEEE, pp. 108-114.

Roundy, S. et al., "A piezoelectric vibration based generator for wireless electronics," Smart Materials and Structures, vol. 13, Issue 5, Aug. 11, 2004, IOP Publishing Ltd, pp. 1131-1142.

Roundy, Shad et al., "A study of low level vibrations as a power source for wireless sensor nodes," Computer Communications, vol. 26, Issue 11, 2003, Elsevier Science B.V., pp. 1131-1144.

Roundy, Shad et al., "Improving Power Output for Vibration-Based Energy Scavengers," IEEE Pervasive Computing, vol. 4, Issue 1, Jan.-Mar. 2005, IEEE, pp. 28-36.

Shenck, Nathan et al., "Energy Scavenging with Shoe-Mounted Piezoelectrics," IEEE Micro, vol. 21, Issue 3, May-Jun. 2001, IEEE, pp. 30-42.

Starner, Thad et al., "Chapter 45: Human Generated Power for Mobile Electronics," Low-Power Electronics Design (book), 2004, CRC Press, pp. 1-30.

Yamamoto, T. et al., "Non-linear electrical properties of skin in the low frequency range," Medical & Biological Engineering & Computing, vol. 19, Issue 3, May 1981, Kluwer Academic Publishers, pp. 302-310.

Yang, Ya et al., "Human Skin Based Triboelectric Nanogenerators for Harvesting Biomechanical Energy and as Self-Powered Active Tactile Sensor System," ACS Nano, vol. 7, Issue 10, Sep. 5, 2013, American Chemical Society, pp. 9213-9222.

Yang, Zhaochu et al., "Power generation from conductive droplet sliding on electret film," Applied Physics Letters, vol. 100, Issue 21, May 23, 2012, American Institute of Physics, pp. 213905-1 through 213905-4.

Zorzi, Michele et al., "From Today's INTRAnet of Things to a Future INTERnet of Things: A Wireless- and Mobility-Related View," IEEE Wireless Communications, vol. 17, Issue 6, Dec. 2010, IEEE, pp. 44-51.

* cited by examiner

US 10,712,879 B2

TOUCH CAPACITANCE TRANSDUCED ENERGY HARVESTING SYSTEM

GOVERNMENT SUPPORT

This invention was made with government funds under Agreement No. HR0011-13-3-0002 awarded by The Defense Advanced Research Projects Agency (DARPA). The U.S. Government has certain rights in this invention.

FIELD OF THE DISCLOSURE

The technology of the disclosure relates generally to energy scavenging in an electronic device.

BACKGROUND

The ever-increasing number of sensor nodes on and around the human body is rapidly transforming the way people interact with their surroundings. The Internet of Things (IoT) has gained considerable traction over the past decade and continued research is forecasted to expand the network to reach from 24 to 50 billion body-worn devices. A perennial obstacle to realizing the deployment of body-worn devices is power. Many body-worn devices may require long operational lifetimes, ideally without the need to replace a battery. Moreover, depending on the application, many sensors may have size and weight constraints, rendering current battery technology inappropriate. Energy harvesting has been seen by many researchers as an emerging solution to meet the power demands of body-worn devices. Of the many ambient sources available, including electromagnetic radiation, thermal gradients, and mechanical motion, solar harvesting is a common choice due to a good balance of power density and packaging flexibility (e.g., enabling form-fitting when recharging wearables).

However, for applications not exposed to sunlight, alternative scavenging sources may be utilized. For example, it may be possible to extract energy from naturally occurring phenomena such as low-level vibrations present in households and office environments and fluidic motion found in evaporation. Unfortunately, small (e.g., centimeter scale or smaller) body-worn devices cannot efficiently make use of ambient environment vibration or fluid flow.

The human body has the potential to be a very valuable source of power for body-worn devices (e.g., biosensors), storing approximately 384 megajoules (MJ) of potential energy in fat for an average sized person. Although most of this chemical energy is not directly harvestable today, a small fraction of the available power can be indirectly scavenged from human temperature gradients and everyday motion. Although the heels of walking shoes are some of the most profitable locations to scavenge energy, it can be difficult to deliver this power to a useful device located somewhere on the body or in the environment. Human finger motion, on the other hand, is a natural means of communication which could generate energy through piezoelectric, triboelectric, and electrostatic transduction.

SUMMARY

Aspects disclosed in the detailed description include a touch capacitance transduced energy harvesting system. The energy harvesting system includes a touch sensing electrode array and energy harvesting circuitry coupled to the touch sensing electrode array. When a movable conductive object (e.g., a human finger) moves toward or away from the touch sensing electrode array, capacitance of the touch sensing electrode array increases and decreases accordingly, thus transducing a direct current (DC) current in the touch sensing electrode array. As such, the energy harvesting circuitry can be configured to harvest electric energy from the DC current to generate and store a DC voltage. By harvesting the electric energy transduced from the kinetic energy of the movable conductive object, it is possible to power a low-power electronic device (e.g., a biosensor) with motions already used for interfacing with the low-power electronic device.

In one aspect, an energy harvesting system is provided. The energy harvesting system includes a touch sensing electrode array. The touch sensing electrode array has a capacitance and is configured to increase the capacitance in response to a movable conductive object being moved toward the touch sensing electrode array. The touch sensing electrode array is also configured to decrease the capacitance in response to the movable conductive object being moved away from the touch sensing electrode array. The energy harvesting system also includes energy harvesting circuitry coupled to the touch sensing electrode array and configured to harvest electric energy from a DC current transduced by the touch sensing electrode array in response to the capacitance being increased and decreased alternately.

In another aspect, a method for harvesting energy is provided. The method includes increasing a capacitance of a touch sensing electrode array by moving a movable conductive object toward the touch sensing electrode array. The method also includes decreasing the capacitance of the touch sensing electrode array by moving the movable conductive object away from the touch sensing electrode array. The method also includes harvesting electric energy from a DC current transduced by the touch sensing electrode array in response to the capacitance being increased and decreased alternately.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1A:
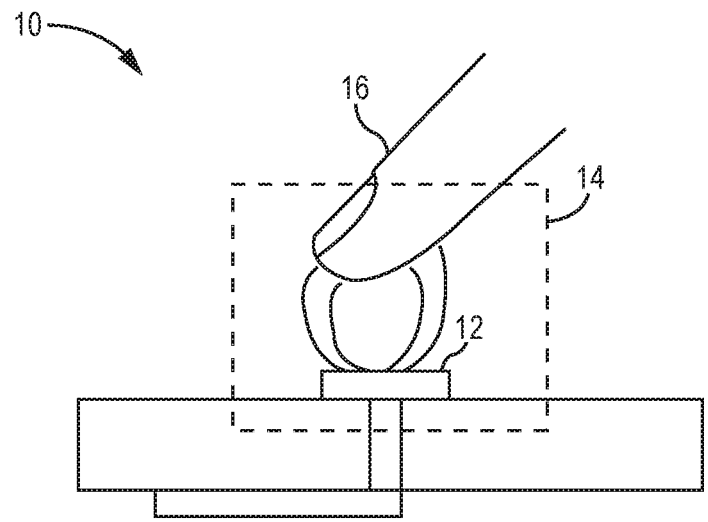
FIG. 1A is a schematic diagram of an exemplary surface capacitive touchpad.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below," "above," "upper," "lower," "horizontal," and/or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Aspects disclosed in the detailed description include a touch capacitance transduced energy harvesting system. The energy harvesting system includes a touch sensing electrode array and energy harvesting circuitry coupled to the touch sensing electrode array. When a movable conductive object (e.g., a human finger) moves toward or away from the touch sensing electrode array, capacitance of the touch sensing electrode array increases and decreases accordingly, thus transducing a direct current (DC) current in the touch sensing electrode array. As such, the energy harvesting circuitry can be configured to harvest electric energy from the DC current to generate and store a DC voltage. By harvesting the electric energy transduced from the kinetic energy of the movable conductive object, it is possible to power a low-power electronic device (e.g., a biosensor) with motions already used for interfacing with the low-power electronic device.

Figure 1B:
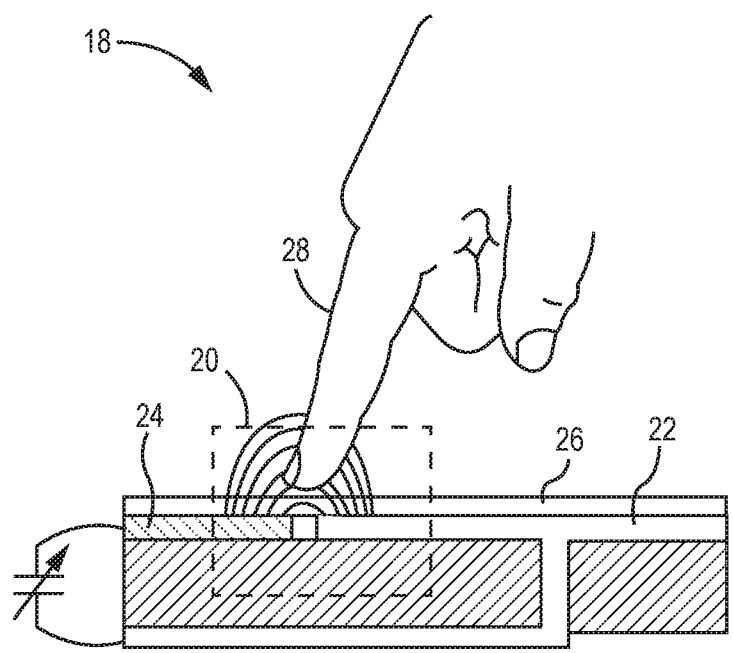
FIG. 1B is a schematic diagram of an exemplary projected capacitive touchpad.

Before discussing the energy harvesting system of the present disclosure, an overview of existing capacitive touch technologies is first provided with reference to FIGS. 1A and 1B. The discussion of specific exemplary aspects of an energy harvesting system starts below with reference to FIG. 2.

Characteristics of a capacitor, which enables existing capacitive touch technologies, can be summarized by the equations (Eq. 1-Eq. 3) below.

$$C = \frac{\varepsilon^* A}{d} \qquad \text{(Eq. 1)}$$

$$Q = C * V \qquad \text{(Eq. 2)}$$

$$i = V * \frac{dC}{dt} + C * \frac{dV}{dt} \qquad \text{(Eq. 3)}$$

In Eq. 1, C represents capacitance of the capacitor, ε represents dielectric permittivity between two conductive plates of the capacitor, A represents overlapping area of the two conductive plates, and d represents the separation distance between the two conductive plates. In this regard, according to Eq. 1, the capacitance C of the capacitor is proportionally related to the dielectric permittivity ε and the overlapping area A, and inversely related to the separation distance d. The capacitance C reflects the capacitor's ability to store an electric charge Q when a voltage V is applied to the two conductive plates of the capacitor. As shown in Eq. 2, the electric charge Q that the capacitor can store is proportionally related to the capacitance C of the capacitor and the voltage V applied to the capacitor. Eq. 3 illustrates that the capacitor can induce a direct current (DC) current i in response to a change in the capacitance C and/or the voltage V. According to Eq. 3, when the voltage V is held steady, the DC current i would increase when the capacitance C increases, and decrease when the capacitance C decreases.

The two existing capacitive touch technologies, namely surface capacitive touch and projected capacitive touch, are both configured to function in response to capacitance changes in a touchpad. A touchpad that functions based on the surface capacitive touch and the projected capacitive touch technologies is discussed next with reference to FIGS. 1A and 1B, respectively.

FIG. 1A is a schematic diagram of an exemplary surface capacitive touchpad 10. The surface capacitive touchpad 10 includes a touch surface 12 that functions as one conductive plate of a capacitor 14, while a human finger 16 forms another conductive plate of the capacitor 14. In this regard, according to Eq. 1, when the human finger 16 moves toward the touch surface 12, capacitance C of the capacitor 14 increases as a result of decreased separation distance d. In contrast, when the human finger 16 moves away from the touch surface 12, the capacitance C of the capacitor 14 decreases as a result of increased separation distance d.

FIG. 1B is a schematic diagram of an exemplary projected capacitive touchpad 18. The projected capacitive touchpad 18 includes at least one capacitor 20 having a first conductive plate 22 and a second conductive plate 24. The first conductive plate 22 serves as a touch sensing electrode. The second conductive plate 24, which is formed by surrounding metal fill, may serve as a ground plane of the projected capacitive touchpad 18. An insulation layer 26 (e.g., parylene or silicon oxide) is deposited above the touch sensing electrode to prevent shorting. In this regard, the overlapping area A and the separation distance d for the capacitor 20 would be fixed. When a voltage V is applied across two conductive plates 22, 24 of the capacitor 20, an electric field exists between the two conductive plates 22, 24. In this regard, when a human finger 28 moves toward the insulation layer 26, the human finger 28 interrupts the electric field between the two conductive plates 22, 24, thus causing the dielectric permittivity ε to increase. As a result, according to Eq. 1, capacitance C of the capacitor 20 would increase. In contrast, when the human finger 28 moves away from the insulation layer 26, the dielectric permittivity ε would decrease. As a result, according to Eq. 1, the capacitance C of the capacitor 20 would decrease as well.

As discussed above in FIGS. 1A and 1B, the capacitance C would increase when a conductive object (e.g., the human finger 16 of FIG. 1A or the human finger 28 of FIG. 1B) approaches a touch surface (e.g., the touch surface 12 of FIG. 1A or the insulation layer 26 of FIG. 1B). In contrast, the capacitance C would decrease when the conductive object moves away from the touch surface. As illustrated in Eq. 3, the changes in the capacitance C can cause the DC current i to increase and decrease accordingly. As such, the DC current i can provide a source for energy scavenging.

Figure 2:
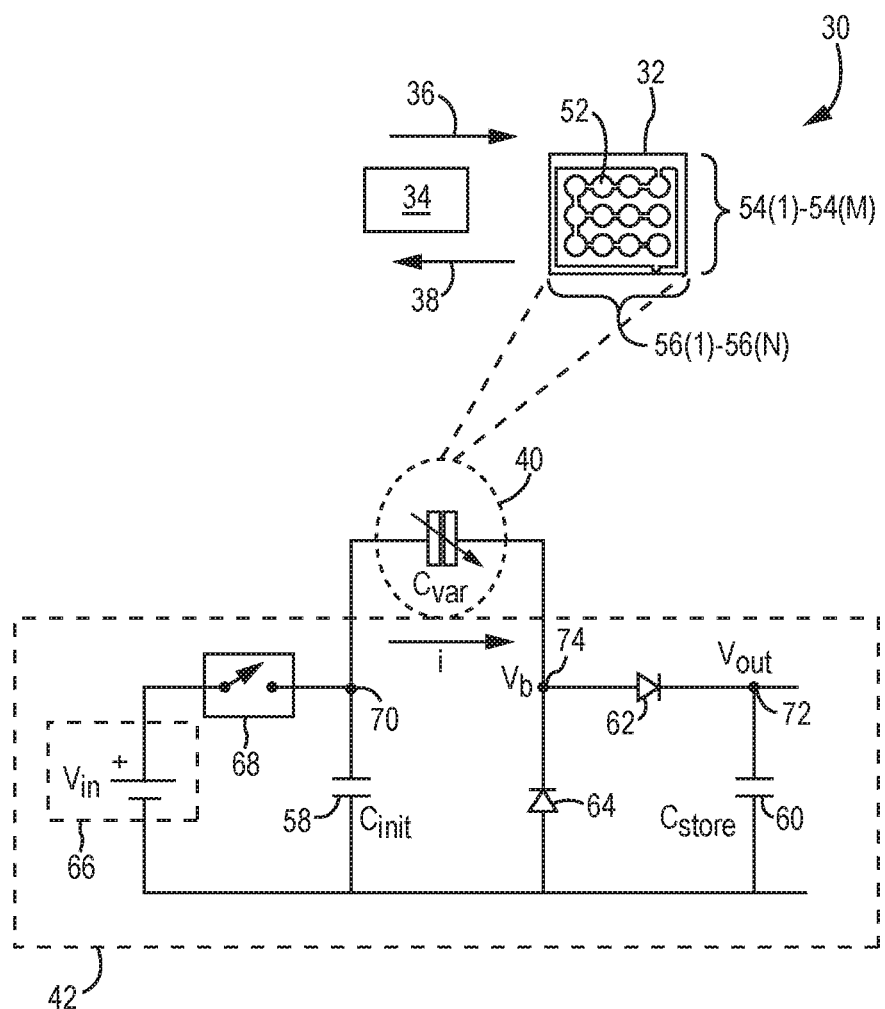
FIG. 2 is a schematic diagram of an exemplary energy harvesting system configured to harvest electric energy transduced from capacitance changes in a touch sensing electrode array.

In this regard, FIG. 2 is a schematic diagram of an exemplary energy harvesting system 30 configured to harvest electric energy transduced from capacitance changes in a touch sensing electrode array 32. In a non-limiting example, the touch sensing electrode array 32 can be a projected capacitive touch (PCT) touchpad or touchscreen that functions based on the projected capacitive touch technology as discussed above in reference to FIG. 1B. As such, the touch sensing electrode array 32 has a capacitance that increases in response to a movable conductive object 34 being moved toward (e.g., closer to) the touch sensing electrode array 32 in direction 36. In contrast, the touch sensing electrode array 32 decreases the capacitance in response to the movable conductive object 34 being moved away from (e.g., farther from) the touch sensing electrode array 32 in direction 38. In this regard, the touch sensing electrode array 32 can be treated as being functionally equivalent to a variable capacitor 40 having a variable capacitance $C_{var}$. Thus, according to Eq. 3 above, the touch sensing electrode array 32 can transduce a DC current i when the capacitance is increased and decreased alternately. Accordingly, it is possible to harvest the electric energy from the DC current I.

The energy harvesting system 30 includes energy harvesting circuitry 42. The energy harvesting circuitry 42 is coupled to the touch sensing electrode array 32. In a non-limiting example, the touch sensing electrode array 32 can be disposed on a top surface of a printed circuit board (PCB), while the energy harvesting circuitry 42 is disposed below the touch sensing electrode array 32 on a bottom surface of the PCB. The energy harvesting circuitry 42 can be configured to harvest the electric energy from the DC current I, which is transduced by the touch sensing electrode array 32 in response to the capacitance being increased and decreased alternately. By harvesting the electric energy from the capacitance changes caused by movement of the movable conductive object 34, the energy harvesting system 30 can transduce the kinetic energy of the movable conductive object 34 to electric energy, thus making it possible to power a low-power electronic device (e.g., a biosensor) with motions already used for interfacing with the low-power electronic device. The energy harvesting system 30 described herein may be employed in any circuit, hardware component, integrated circuit (IC), or IC chip, as examples.

Figure 3:
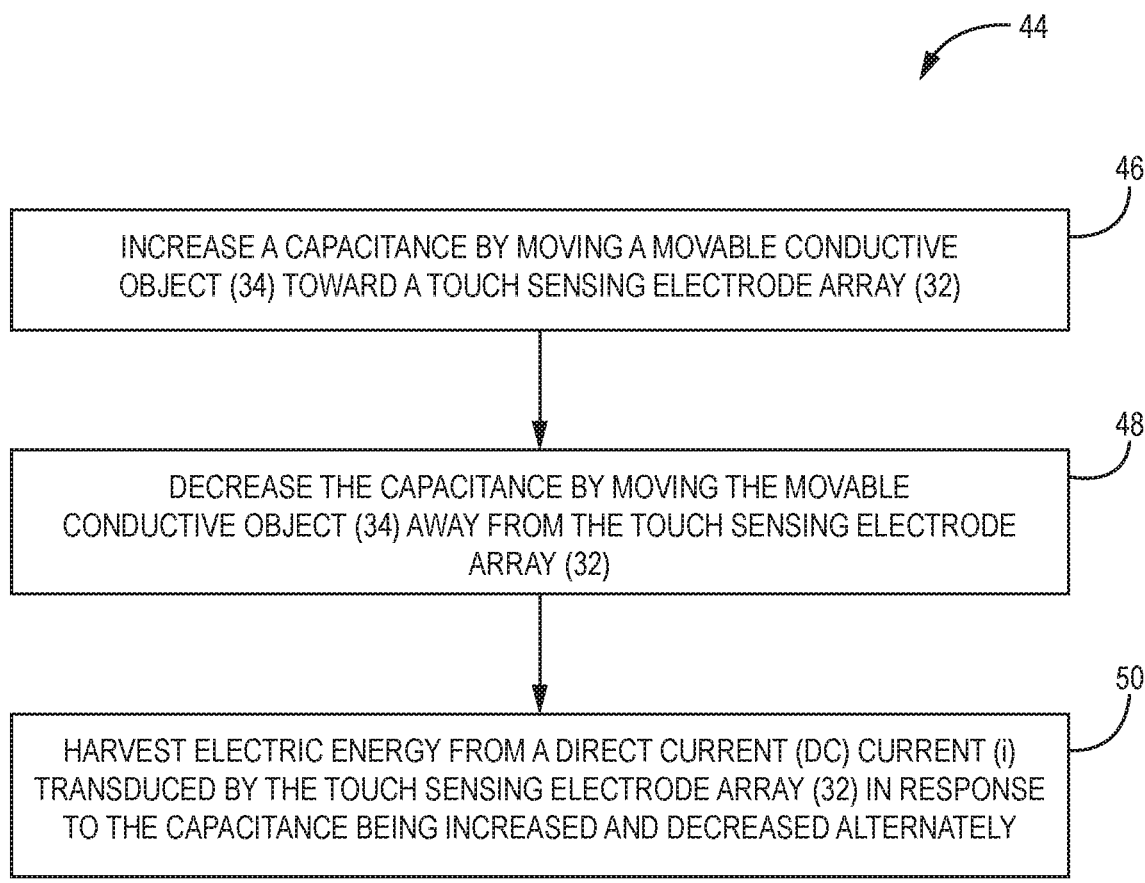
FIG. 3 is a flowchart of an exemplary process that can be employed by the energy harvesting system of FIG. 2 to harvest the electric energy transduced from the capacitance changes in the touch sensing electrode array.

The energy harvesting system 30 may be configured to harvest the electric energy according to a process. In this regard, FIG. 3 is a flowchart of an exemplary process 44 that can be employed by the energy harvesting system 30 of FIG. 2 to harvest the electric energy transduced from capacitance changes in a touch sensing electrode array 32.

According to the process 44, the touch sensing electrode array 32 increases the capacitance when the movable conductive object 34 is moved toward the touch sensing electrode array 32 (block 46). Further, the touch sensing electrode array 32 decreases the capacitance when the movable conductive object 34 is moved away from the touch sensing electrode array 32 (block 48). The energy harvesting circuitry 42 harvests the electric energy from the DC current i transduced by the touch sensing electrode array 32 in response to the capacitance being increased and decreased alternately (block 50). In a non-limiting example, the movable conductive object 34 can be moved toward the touch sensing electrode array 32 to cause the increased capacitance and then moved away from the touch sensing electrode array 32 to cause the decreased capacitance within one second (1 s). As such, the increased capacitance and the decreased capacitance alternate every one-half second (0.5 s).

With reference back to FIG. 2, in one non-limiting example, the touch sensing electrode array 32 can increase the capacitance when the movable conductive object 34 is in physical contact with the touch sensing electrode array 32, and decrease the capacitance when the movable conductive object 34 is out of physical contact with the touch sensing electrode array 32. According to previous discussions in FIG. 1B, an insulation layer is deposited above the touch sensing electrode array 32 to prevent shorting. As such, whenever the movable conductive object 34 is said to be in physical contact with the touch sensing electrode array 32, the movable conductive object 34 would actually contact the insulation layer of the touch sensing electrode array 32, as opposed to contacting the touch sensing electrode array 32 directly. In another non-limiting example, the touch sensing electrode array 32 can increase the capacitance when the movable conductive object 34 is placed in close proximity with the touch sensing electrode array 32 by being separated from the touch sensing electrode array 32 by less than a defined distance. In contrast, the touch sensing electrode array 32 can decrease the capacitance when the movable conductive object 34 is separated from the touch sensing electrode array 32 by more than the defined distance. Notably, capacitance variations ΔC caused by physically contacting the touch sensing electrode array 32 may be larger compared to the capacitance variations ΔC caused by placing the movable conductive object 34 in close proximity with the touch sensing electrode array 32. Accordingly, based on Eq. 3, more DC current i may be generated and more electric energy may be harvested.

The touch sensing electrode array 32 may be embedded in an electronic device (e.g., a biosensor) or placed on any object that is within reach of the movable conductive object 34. In a non-limiting example, the touch sensing electrode array 32 can be adhered to human skin or implanted underneath human skin. In this regard, the movable conductive object 34 may be a movable human body part (e.g., finger, toe, elbow, palm, fist, etc.). Furthermore, the movable conductive object 34 may also be a conductive stylus held in a human hand. Accordingly, the touch sensing electrode array 32 may increase the capacitance by moving the movable human body part toward or by placing the movable human body part in physical contact with the touch sensing electrode array 32. The touch sensing electrode array 32 may decrease the capacitance by moving the movable human body part away from or by taking the movable human body part out of physical contact with the touch sensing electrode array 32.

The touch sensing electrode array 32 can be fabricated to include a plurality of electrodes 52 organized into a plurality of rows 54(1)-54(M) and a plurality of columns 56(1)-56(N). Although the electrodes 52 are shown therein as circular shapes, it should be appreciated that the electrodes 52 can be in other suitable shapes (e.g., triangular-shaped, rectangular-shaped, octagonal-shaped, etc.) as well. In a non-limiting example, the touch sensing electrode array 32 includes twelve gold circular electrodes each having a 500 micrometer (μm) radius. The twelve gold circular electrodes may be formed by twelve capacitors with 100 μm separation distance d between the two conductive plates. The twelve gold circular electrodes may be organized into three (3) rows and four (4) columns, with 350 μm between each of the twelve gold circular electrodes, thus allowing for scaling the effect of the changing capacitance among the twelve capacitors. The twelve capacitors can fit into an area measuring 6×5 square millimeters (mm²), thus comfortably covering an area under a pad of a human finger. The twelve capacitors may be provided on a topside of a standard FR4 PCB.

The energy harvesting circuitry 42, which may be disposed on a backside (opposite of the topside) of the FR4 PCB, includes a first capacitor 58, a second capacitor 60, a first diode 62, and a second diode 64. During operation of the energy harvesting circuitry 42, the first capacitor 58 has a first capacitance $C_{init}$ and is charged by a power source 66 configured to provide a bias voltage $V_{in}$ (e.g., five volts (5 V)). In a non-limiting example, the power source 66 can be an electret or a solar-based power source. The power source 66 is coupled to the first capacitor 58 by a switch 68 to charge the first capacitor 58 to the bias voltage $V_{in}$ at a first coupling point 70.

As the variable capacitor 40, which represents the touch sensing electrode array 32, increases the variable capacitance $C_{var}$ due to the movable conductive object 34 being moved toward the touch sensing electrode array 32, voltage across the variable capacitor 40 would decrease, creating a positive bias voltage $V_b$ at a third coupling point 74. The positive bias voltage $V_b$ turns on the first diode 62 to transfer electric charges from the variable capacitor 40 to the second capacitor 60. As such, the energy harvesting circuitry 42 harvests the electric energy generated by the variable capacitor 40 and generates a DC voltage $V_{out}$ based on the harvested electric energy. The energy harvesting circuitry 42 stores the DC voltage $V_{out}$ in the second capacitor 60. The actual value of the DC voltage $V_{out}$ is dependent on the electric charge that passes through the first diode 62 and a second capacitance $C_{store}$ of the second capacitor 60. Operations of the energy harvesting circuitry 42 in response to the movable conductive object 34 approaching the touch sensing electrode array 32 can be summarized in the equations (Eq. 4-Eq. 7) below.

$$\frac{dCvar}{dt} > 0 \tag{Eq. 4}$$

$$I(t) = V_{in} * \left(\frac{dCvar}{dt}\right) \tag{Eq. 5}$$

$$dQ = \int I(t)dt \tag{Eq. 6}$$

$$dV_{out} = \int I(t)dt / C_{store} \tag{Eq. 7}$$

When the movable conductive object 34 departs from the touch sensing electrode array 32, the positive voltage $V_b$ at the third coupling point 74 decreases. As a result, the first diode 62 is turned off to prevent the second capacitor 60 from discharging the DC voltage $V_{out}$. The total electric energy $E_{total}$ stored in the energy harvesting circuitry 42 equals the electric energy stored in the first capacitor 58, the second capacitor 60, and the variable capacitor 40, as expressed in the equations (Eq. 8-Eq. 10) below.

$$E = \frac{1}{2}(C*V^2) \tag{Eq. 8}$$

$$E_{total} = \frac{1}{2}[C_{init}*V_{in}^2 + C_{var}*(V_{in}-V_b)^2 + C_{store}*V_{out}^2] \tag{Eq. 9}$$

$$\Delta E = \frac{1}{2}(C_{store}*V_{out}^2) \tag{Eq. 10}$$

Figure 4:
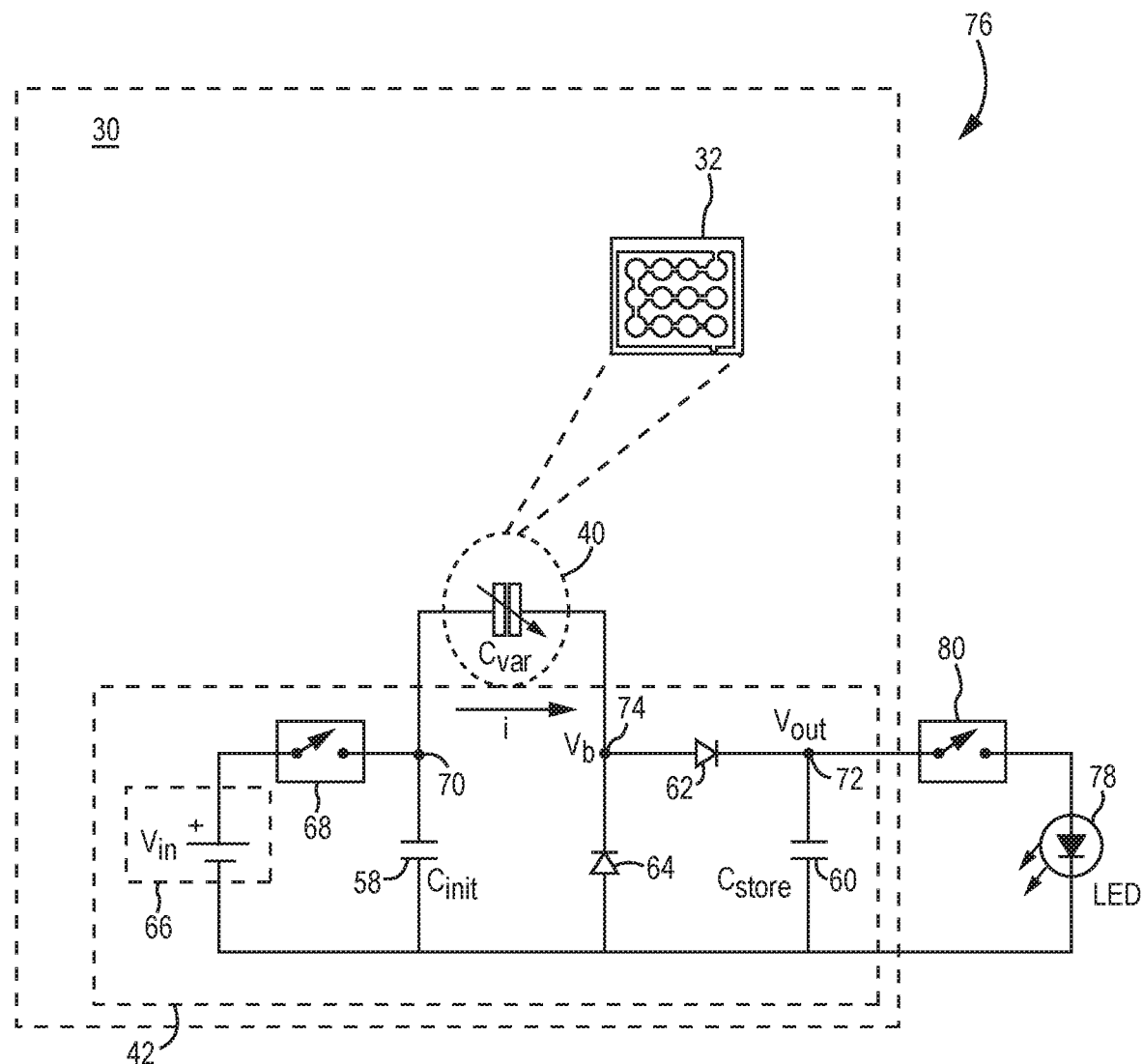
FIG. 4 is a schematic diagram of an exemplary evaluation system for simulating and evaluating the energy harvesting system of FIG. 2.

In an exemplary experiment, the energy harvesting system 30 is evaluated with Cadence Spectre Simulator. In this regard, FIG. 4 is a schematic diagram of an exemplary evaluation system 76 for simulating and evaluating the energy harvesting system 30 of FIG. 2. Common elements between FIGS. 2 and 4 are shown therein with common element numbers and will not be re-described herein.

Figure 5A:
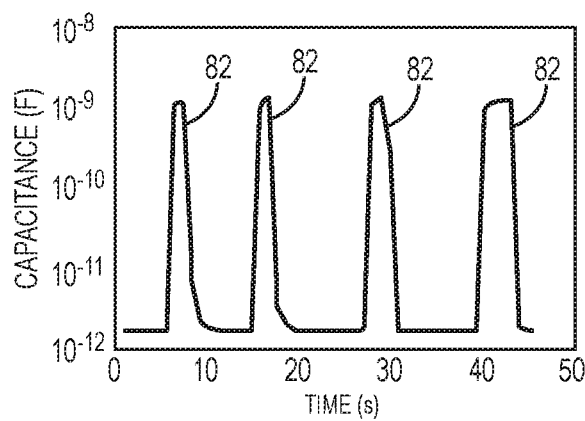
FIGS. 5A-5B are exemplary plots summarizing evaluation results associated with moving a movable conductive object toward and away from a touch sensing electrode array in the evaluation system of FIG. 4.
Figure 5B:
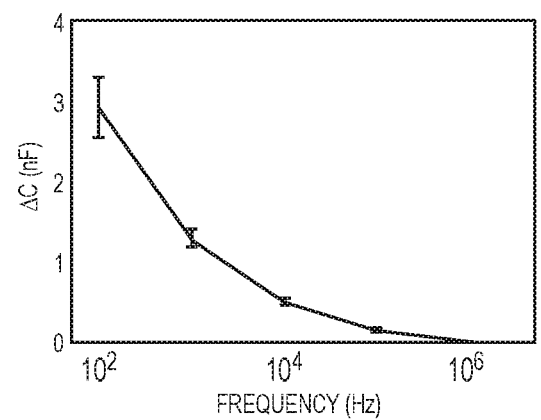

In the evaluation system 76, the energy harvesting circuitry 42 is coupled to a light-emitted diode (LED) 78 via a second switch 80. The capacitance change of the touch sensing electrode array 32 is measured using a Hewlett Packard 4428A inductance, capacitance, and resistance (LCR) meter. The DC voltage $V_{out}$ and the positive bias voltage $V_b$ can be measured by buffering the second coupling point 72 and the third coupling point 74 with an ultra-low input current amplifier (e.g., Texas Instruments, LMC6001) and recorded with either an Agilent 3440A digital multimeter or a Keithley 2400 sourcemeter. To determine the electric power harvested from the energy harvesting circuitry 42 without interrupting the energy harvesting system 30, silicon photodiodes (Open System Interconnect (OSI) Optoelectronic, S-10C) is used to measure the intensity of light emitted from the LED 78. FIGS. 5A-5B are exemplary plots summarizing evaluation results associated with moving the movable conductive object 34 toward and away from the touch sensing electrode array 32 in the evaluation system 76 of FIG. 4.

FIG. 5A illustrates the capacitance variations ΔC of the variable capacitor 40 resulting from a plurality of taps 82 on the touch sensing electrode array 32 by a human finger at a tapping frequency of 1 kilohertz (KHz). At such trapping frequency, the variable capacitance $C_{var}$ increases from a nominal 1.7 picoFarad (pF) to 1.5 nanoFarad (nF). The capacitance variations ΔC of nearly 900 times is significantly larger than a two times increase reported from a 20 kilopascal (KPa) finger pressure on piezoelectrics and a seven to ten times capacitance increase reported from microfluidic-enabled energy harvesting systems.

FIG. 5B shows that detectability of the capacitance variations ΔC decays with measurement frequency on the LCR meter. As the measurement frequency decreases, the variable capacitance $C_{var}$ increases non-linearly and the capacitance variations ΔC also increase. Note that the energy harvesting system 30 configured to harvest the electric energy from the capacitance variations ΔC will operate at relatively low frequencies with respect to changes on the energy harvesting circuitry 42. The capacitance variations ΔC at such low frequencies may not be measured due to limitations of the LCR meter, but can be extrapolated, resulting in a maximum capacitance of approximately 6 nF at DC. The frequency's dependence on the effect of finger proximity is expected since charge re-distribution caused by the human finger is also frequency dependent.

Figure 5C:
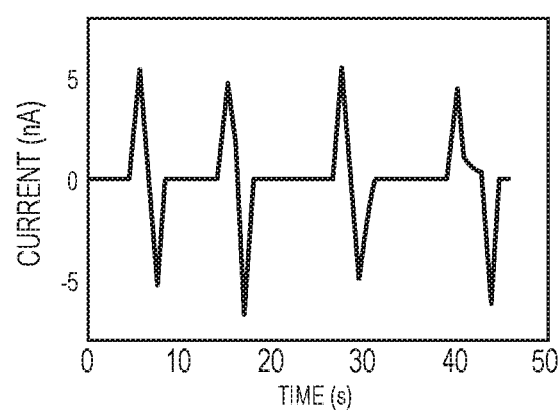
FIGS. 5C-5D are exemplary plots showing simulated currents as a result of detected capacitance changes in FIGS. 5A-5B.
Figure 5D:
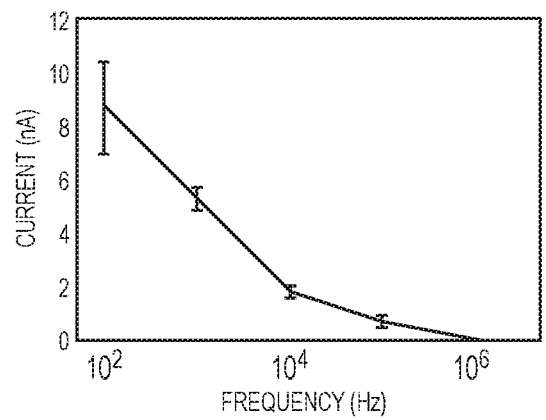

FIGS. 5C-5D are exemplary plots showing simulated currents as a result of detected capacitance changes in FIGS. 5A and 5B. FIG. 5C shows that the DC current i generated as a result of the taps 82 is a function of time at the 1 KHz tapping frequency. As shown in FIG. 5C, the capacitance variations ΔC result in approximately 5.9 nanoAmps (nA) of current.

FIG. 5D shows that the DC current i generated as a result of the taps 82 is also a function of the measurement frequency. The DC current i is inversely related to the measurement frequency. As a result, the DC current i increases at lower measurement frequencies. According to FIG. 5D, the DC current i can vary from 9 nA to 0.12 nA over a 100 Hz to 1 megahertz (MHz) range of the measurement frequency.

Notably, the energy harvesting system 30 should be designed with large margins with respect to the capacitance variations ΔC to accommodate variations in finger position during normal tapping (e.g., offset the tap from the center of the touch sensing electrode array 32 or discrepancies in finger geometrics and composition). In addition, especially in a lossy system, it may be imperative to ensure that the capacitance variations ΔC overcome the natural decay of the second capacitor 60 via unavoidable leakage resistances to ground.

FIGS. 6A-6D are plots providing exemplary illustrations of simulated performance results of the energy harvesting system 30 of FIG. 2. Elements in FIG. 2 are referenced in conjunction with FIGS. 6A-6D and will not be re-described herein.

Figures 6A, 6B, 6C, 6D:
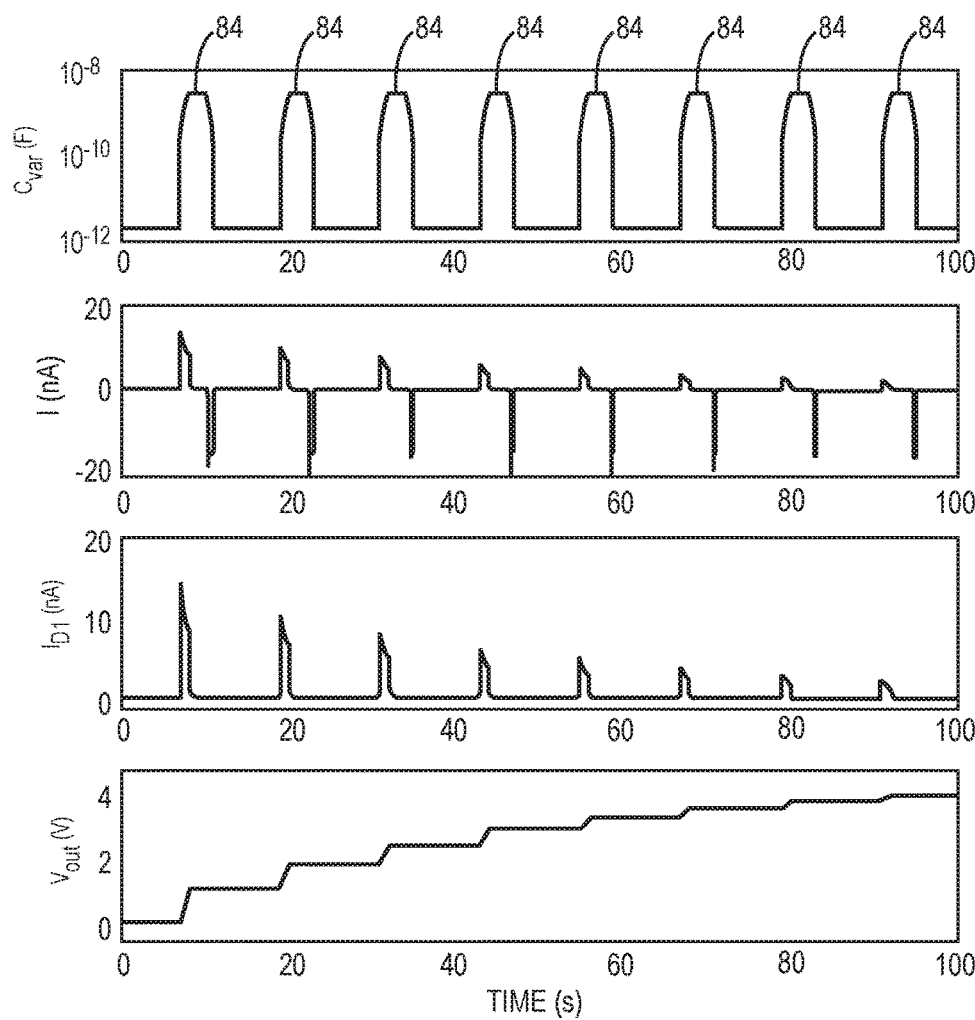
FIGS. 6A-6D are plots providing exemplary illustrations of simulated performance results of the energy harvesting system of FIG. 2.

FIG. 6A shows a waveform of the variable capacitance Cvar that is reflective of the capacitance variations ΔC from a plurality of finger taps 84 on the touch sensing electrode array 32. The capacitance variations ΔC resulting from the finger taps 84 may be between 1.5 pF and 2.9 nF with rise and fall times of 1 second.

FIG. 6B shows the DC current i flowing through the variable capacitor 40. In response to each of the finger taps 84, electric charge is transferred from the variable capacitor 40 to the second capacitor 60 via the first diode 62, resulting in a step increase in the DC voltage $V_{out}$ at the second coupling point 72. The DC current i reflects the electric charge transfer decreasing with subsequent taps due to the increase of the DC voltage $V_{out}$, which decreases the positive bias voltage $V_b$ across the first diode 62.

FIG. 6C shows the DC current i as rectified by the first diode 62. The DC current i that passes through the first diode 62 will also decrease with subsequent taps due to the increase of the DC voltage $V_{out}$, which decreases the positive bias voltage $V_b$ across the first diode 62. The decrease in the positive bias voltage $V_b$ causes current flowing through the first diode 62 to decrease, thus limiting the DC voltage $V_{out}$ to which the second capacitor 60 can be charged.

FIG. 6D shows that the DC voltage $V_{out}$ rises over time as a result of the second capacitor 60 being charged up. In the event that more energy is required, it may be possible to configure the energy harvesting system 30 to pre-charge the first capacitor 58 via a higher input voltage $V_{in}$ and/or increase the second capacitance $C_{store}$ of the second capacitor 60. Although it is possible to increase the harvested energy by increasing the second capacitance $C_{store}$, it will also require a longer time to charge up the second capacitor 60 to the desired DC voltage $V_{out}$. Such tradeoffs may need to be considered when designing the energy harvesting system 30 for a specific application. In addition, it is shown with the arrangement of the first diode 62 and the second diode 64 in the energy harvesting circuitry 42 that a negative capacitance variation would not discharge the second capacitance $C_{store}$ of the second capacitor 60. Based on the simulated results shown in FIGS. 6A-6D, when the second capacitor 60 is completely discharged, taps on the touch sensing electrode array 32 would result in approximately 5 nanoJoules (nJ) of harvested electric energy.

Figure 7A:
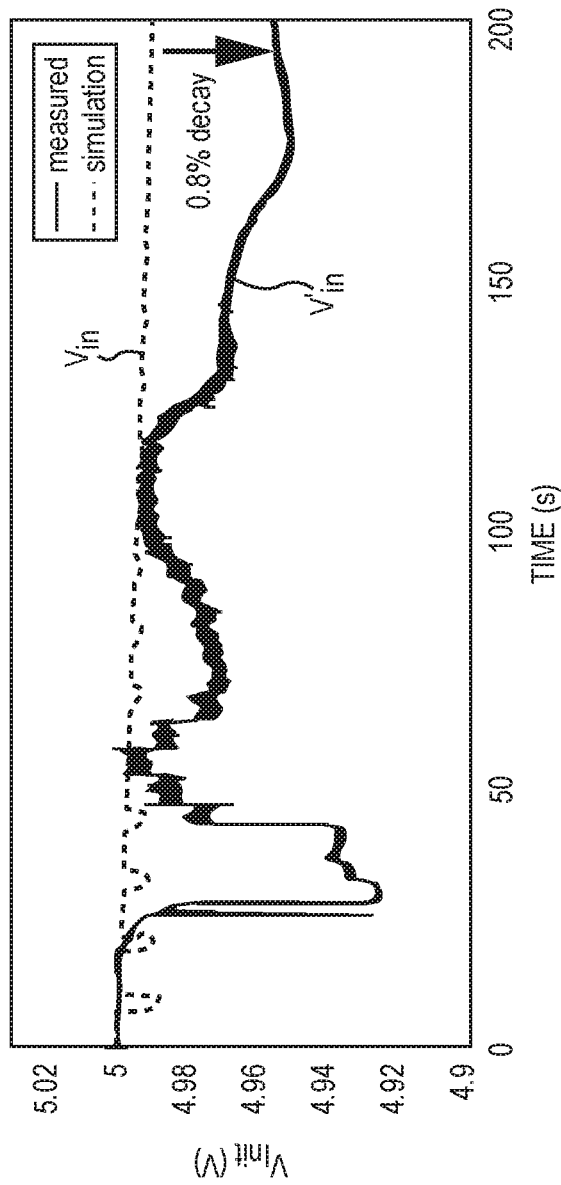
FIGS. 7A-7B are exemplary plots summarizing voltage measurements obtained via the evaluation system of FIG. 4.
Figure 7B:
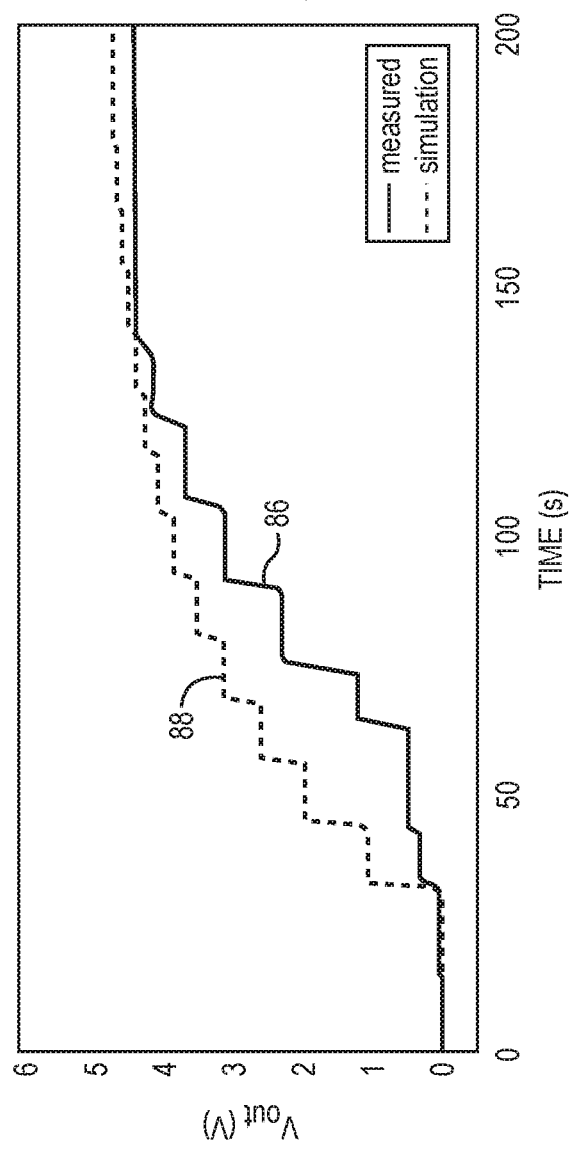

FIGS. 7A-7B are exemplary plots summarizing voltage measurements obtained via the evaluation system 76 of FIG. 4. FIG. 7A shows measured input voltage $V'_{in}$ as compared with simulated input voltage $V_{in}$ over time. As shown in FIG. 7A, the measured input voltage $V'_{in}$ deviates from the simulated input voltage $V_{in}$ and decays quickly. There is a more rapid decay in the simulated input voltage $V_{in}$ as a result of the fact that parallel resistance to ground may not be adequately represented in the simulation.

FIG. 7B shows a measured DC voltage curve 86 and a simulated DC voltage curve 88. FIG. 7B shows that each tap contributes to the staircase charging pattern of the second capacitor 60 in both the measured DC voltage curve 86 and the simulated DC voltage curve 88. The measured DC voltage as illustrated by the measured DC voltage curve 86 saturates at a maximum voltage below the simulated DC voltage curve 88, which may be arbitrated to losses in the simulated input voltage $V_{in}$. Notably, there is much more variability in the electric energy harvested from each tap because human error makes it difficult to identically reproduce the same capacitance variations ΔC in actual measurement. Due to the losses in the simulated input voltage $V_{in}$ and finger variability, the actual electric energy harvested is closer to 1 nJ per tap.

Figure 8A:
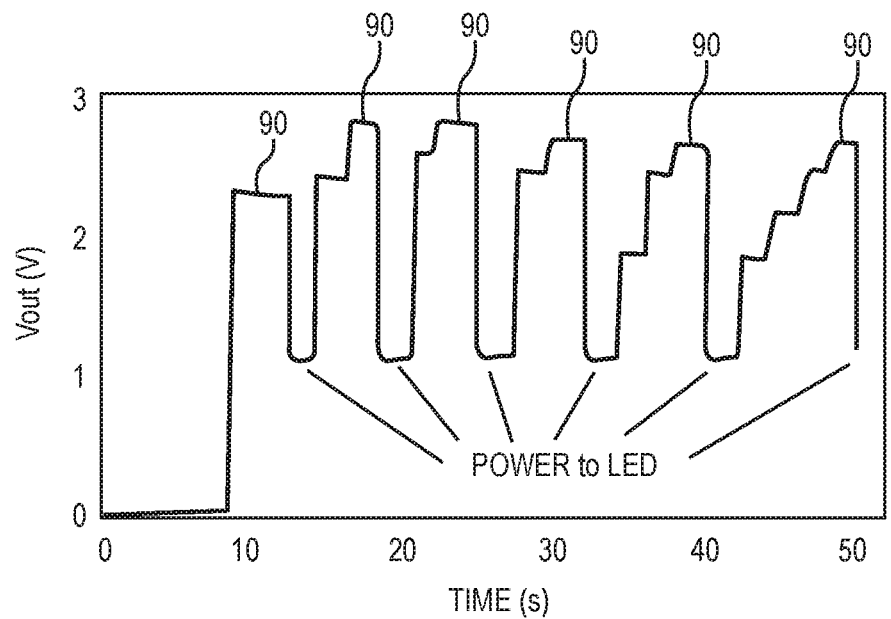
FIGS. 8A-8B are plots providing exemplary results of evaluations conducted via the evaluation system of FIG. 4.
Figure 8B:
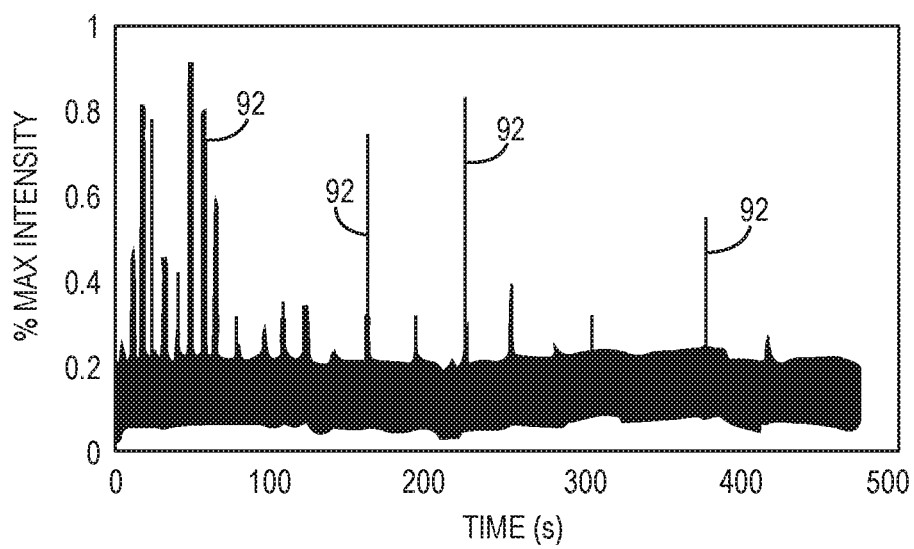

FIGS. 8A-8B are plots providing exemplary results of evaluations conducted via the evaluation system 76 of FIG. 4. The evaluation system 76 of FIG. 4 demonstrates that the electric energy harvesting system 30 can repeatedly power the LED 78. FIG. 8A shows that profile for the DC voltage $V_{out}$ as the second capacitor 60 is charged up with multiple taps 90, and then discharges through the LED 78 when the second switch 80 is closed.

To ensure there is no current injection or leakage into the measurement devices (e.g., the LCR meter and the amplifiers) during the evaluation, LED output is tracked by measuring light intensity of the LED 78 via a photodiode. The intensity of the light is, in first order, proportional to how much power is drawn through the LED 78. As shown in FIG. 8B, over a 500 second time frame, intermittent tapping provides enough electric energy to illuminate the LED 78 for brief periods of time, as seen by the spikes 92 in FIG. 8B.

Using the relationship between intensity and power, comparing the power extracted from the initially charged first capacitance $C_{init}$ of the first capacitor 58 with power extracted from the second capacitor 60, it may be able to determine that over 500 seconds, approximately 2.5 times more useful power is harvested for the LED 78 than the power initially presented in the evaluation system 76 at startup. The evaluation system 76 demonstrates that the electric energy harvesting system 30 can harvest electric energy from tactile motion to periodically power such load as the LED 78.

Those skilled in the art will recognize improvements and modifications to the preferred embodiments of the present disclosure. All such improvements and modifications are considered within the scope of the concepts disclosed herein and the claims that follow.

What is claimed is:

1. An energy harvesting system comprising:
   a touch sensing electrode array having a capacitance and configured to:
   increase the capacitance in response to a movable conductive object being moved toward the touch sensing electrode array; and
   decrease the capacitance in response to the movable conductive object being moved away from the touch sensing electrode array; and
   energy harvesting circuitry coupled to the touch sensing electrode array and configured to harvest electric energy from a direct current (DC) current transduced by the touch sensing electrode array in response to the capacitance being increased and decreased alternately.

2. The energy harvesting system of claim 1 wherein the energy harvesting circuitry is further configured to generate and store a DC voltage based on the harvested electric energy.

3. The energy harvesting system of claim 1 wherein the touch sensing electrode array is configured to:
   increase the capacitance when the movable conductive object is in physical contact with the touch sensing electrode array; and
   decrease the capacitance when the movable conductive object is out of physical contact with the touch sensing electrode array.

4. The energy harvesting system of claim 1 wherein the touch sensing electrode array is configured to:
   increase the capacitance when the movable conductive object is separated from the touch sensing electrode array by less than a defined distance; and
   decrease the capacitance when the movable conductive object is separated from the touch sensing electrode array by more than the defined distance.

5. The energy harvesting system of claim 1 wherein the touch sensing electrode array is configured to:
   increase the capacitance in response to a movable human body part being moved toward the touch sensing electrode array; and
   decrease the capacitance in response to the movable human body part being moved away from the touch sensing electrode array.

6. The energy harvesting system of claim 1 wherein the touch sensing electrode array is configured to:
   increase the capacitance in response to a human finger being moved toward the touch sensing electrode array; and
   decrease the capacitance in response to the human finger being moved away from the touch sensing electrode array.

7. The energy harvesting system of claim 1 wherein the touch sensing electrode array is configured to:
   increase the capacitance in response to a conductive stylus held in a human hand being moved toward the touch sensing electrode array; and
   decrease the capacitance in response to the conductive stylus being moved away from the touch sensing electrode array.

8. The energy harvesting system of claim 1 wherein the touch sensing electrode array comprises a projected capacitive touch (PCT) touchpad.

9. The energy harvesting system of claim 1 wherein the touch sensing electrode array comprises a plurality of electrodes organized into a plurality of rows and a plurality of columns.

10. The energy harvesting system of claim 1 provided in an integrated circuit (IC).

11. The energy harvesting system of claim 1 wherein the energy harvesting circuitry comprises an electret configured to provide a bias voltage to the energy harvesting circuitry.

12. The energy harvesting system of claim 1 wherein the energy harvesting circuitry comprises a solar-based power source configured to provide a bias voltage to the energy harvesting circuitry.

13. A method for harvesting energy comprising:
   increasing a capacitance of a touch sensing electrode array by moving a movable conductive object toward the touch sensing electrode array;
   decreasing the capacitance of the touch sensing electrode array by moving the movable conductive object away from the touch sensing electrode array; and
   harvesting electric energy from a direct current (DC) current transduced by the touch sensing electrode array in response to the capacitance being increased and decreased alternately.

14. The method of claim 13 further comprising generating and storing a DC voltage based on the harvested electric energy.

15. The method of claim 13 further comprising:
   increasing the capacitance when the movable conductive object is in physical contact with the touch sensing electrode array; and
   decreasing the capacitance when the movable conductive object is out of physical contact with the touch sensing electrode array.

16. The method of claim 13 further comprising:
increasing the capacitance when the movable conductive object is separated from the touch sensing electrode array by less than a defined distance; and
decreasing the capacitance when the movable conductive object is separated from the touch sensing electrode array by more than the defined distance.

17. The method of claim 13 further comprising:
increasing the capacitance by moving a movable human body part toward the touch sensing electrode array; and
decreasing the capacitance by moving the movable human body part away from the touch sensing electrode array.

18. The method of claim 13 further comprising:
increasing the capacitance by moving a human finger toward the touch sensing electrode array; and
decreasing the capacitance by moving the human finger away from the touch sensing electrode array.

19. The method of claim 13 further comprising:
increasing the capacitance by moving a conductive stylus held in a human hand toward the touch sensing electrode array; and
decreasing the capacitance by moving the conductive stylus away from the touch sensing electrode array.

20. The method of claim 13 further comprising:
increasing the capacitance by moving the movable conductive object toward a projected capacitive touch (PCT) electrode array; and
decreasing the capacitance by moving the movable conductive object away from the PCT electrode array.

\* \* \* \* \*